United States Patent [19]

Reilly

[11] Patent Number: 5,514,601
[45] Date of Patent: May 7, 1996

[54] DETECTION OF TARGET SPECIES IN A SAMPLE OR LIQUID FLOW USING DIODES AND AN ELECTRICAL SIGNAL

[75] Inventor: Paul J. Reilly, Hardwick, Great Britain

[73] Assignee: Boehringer Mannheim GmbH, Mannheim, Germany

[21] Appl. No.: 372,902

[22] Filed: Jan. 17, 1995

Related U.S. Application Data

[63] Continuation of Ser. No. 104,159, filed as PCT/GB92/00329, Feb. 22, 1991, abandoned.

[30] Foreign Application Priority Data

Feb. 22, 1991 [GB] United Kingdom ............... 9103752

[51] Int. Cl.$^6$ .............................. G01N 33/543
[52] U.S. Cl. .............. 436/518; 73/61.41; 73/61.71; 204/113; 204/400; 204/403; 324/76.11; 422/82.01; 422/82.02; 435/287.2; 435/287.1; 435/817; 436/149; 436/150; 436/524; 436/525; 436/806; 436/807
[58] Field of Search ................. 204/193, 400, 204/403; 422/82.01, 82.02; 435/287, 291, 817; 436/149, 150, 518, 524, 525, 806, 807; 73/61.41, 61.71; 324/76.11

[56] References Cited

U.S. PATENT DOCUMENTS

| | | | |
|---|---|---|---|
| 4,219,335 | 8/1980 | Ebersole | 436/806 |
| 4,240,027 | 12/1980 | Larsen et al. | 324/57 R |
| 4,713,347 | 12/1987 | Mitchell et al. | 436/806 |
| 4,801,543 | 1/1989 | Arnold et al. | 436/806 |
| 4,935,207 | 6/1990 | Stanbro et al. | 435/817 |
| 5,002,884 | 3/1991 | Kobayashi et al. | |
| 5,074,977 | 12/1991 | Cheung et al. | 436/806 |
| 5,162,238 | 11/1992 | Eikmeier et al. | |

FOREIGN PATENT DOCUMENTS 8802115  3/1988  United Kingdom.

OTHER PUBLICATIONS

RCA Designer's Handbook, "Solid-State Power Circuits", Technical Series SP-52, Sep. 1971.

Primary Examiner—James C. Housel
Assistant Examiner—Christopher L. Chin
Attorney, Agent, or Firm—Nikaido, Marmelstein, Murray & Oram

[57] ABSTRACT

A method of and apparatus for the presence of a target species in a sample taken from or consisting of a mixture of species, comprising the steps of introducing one or more electrical diodes into the mixture prior to taking the sample from the mixture, in such a manner that the presence of diodes in the sample is dependent on the presence of the target species in the sample; passing an alternating electrical signal having a known waveform through the sample; and detecting the modification of the waveform of the signal emerging from the sample due to the presence of the diode or diodes in the sample.

23 Claims, 7 Drawing Sheets

DETECTION OF TARGET SPECIES IN A SAMPLE OR LIQUID FLOW USING DIODES AND AN ELECTRICAL SIGNAL

This application is a continuation of application Ser. No. 08/104,159, filed Aug. 20, 1993, now abandoned which is a 371 of PCT/GB92/003292/241.

FIELD OF THE INVENTION

This invention relates to a method and apparatus for the detection of a target species in a sample.

BACKGROUND TO THE INVENTION

In many chemical or biochemical reaction situations, it is necessary to detect the presence in a mixture of species of a particular target species. For example, in immunological assay reactions, it is necessary to be able to accurately detect the presence of, often very small, quantities of a particular antibody or other biochemical species.

Known methods for detecting a target species in a sample, particularly in biochemical reactions, often involve introducing into the sample a reagent which will react specifically with the target species. Once this reagent has combined with any target species present in the sample, the presence of the reagent-target pair is then detected in a number of known ways. For instance, the reagent may be labelled in some way (chemically or radioactively, for example) to allow for ease of its detection.

One particular case in which reliable detection methods are necessary is the detection of a particular antibody in a sample. Here, the reagent introduced into the sample is a specific antigen which binds to target antibody present in the sample. The presence of the antigen-antibody pair in the sample can then be detected.

Alternatively, a particular antigen may be the target species to be detected, in which case the reagent introduced into the sample is a specific antibody which binds to the target antigen.

A number of known detection methods make use of some characteristic of the antigen. For example, the technique of "latex agglutination" makes use of antigen-coated bodies whose increase in aggregate size following binding to the target antibody can be detected optically. Radioactive markers and fluorescent dyes have also been used to "label" the antigen and allow its detection following binding to the target antibody.

These known detection methods have undesirable characteristics. Any macro-scale technique (such as latex agglutination) inevitably requires large numbers of antigen-antibody pairs to be present in a sample to produce a detectable effect. Fluorescent and radioactive markers are difficult and expensive to detect with the required sensitivity.

These difficulties are often paralleled in other chemical and biochemical reaction situations where sensitive and reliable detection methods are needed.

The need for a reliable method for detection of a target species in a sample also arises in the monitoring of fluid flow through a system or of particle movement through a fluid system; and in the detection of fluid leaks from a system. In each case, a sample is taken from a particular location inside or outside the system and the presence of a Larger species in that sample detected, which then provides information as to which areas of the system the target has reached or, as the case may be, whether the target has been able to leak out of the system. In these cases, too, there is always a need for a simpler, more reliable and more sensitive detection method than those currently available.

STATEMENT OF THE INVENTION

According to the present invention there is provided a method of detecting the presence of a diode in a sample taken from a mixture, into which mixture the diode has previously been introduced, comprising the steps of passing an alternating electrical signal having a known waveform through the sample, and detecting the modification of the waveform of the signal emerging from the sample due to the presence of the diode in the sample.

More specifically there is provided according to the present invention a method of detecting the presence of a target species in a sample taken from or consisting of a mixture of species, comprising the steps of introducing one or more electrical diodes into the mixture prior to taking the sample from the mixture, in such a manner that the presence of diodes in the sample is dependent on the presence of the target species in the sample; passing an alternating electrical signal having a known waveform through the sample; and detecting the modification of the waveform of the signal emerging from the sample due to the presence of a diode or diodes in the sample.

The invention is based on the discovery that an alternating electrical signal passed through an electrically conductive medium will be modified if one or more electrical diodes is present in that medium, and specifically on the realization that this phenomenon can be utilized for the detection of target species in a sample provided the presence of diodes in the sample can be made dependent on the presence of the target species in the sample.

The method of the invention can thus make use of relatively low-cost apparatus to allow for very sensitive detection of a target species.

The electrical diode or diodes will each comprise any body capable of exhibiting a diode effect when alternating current is passed through it. A simple lump of a PN-doped semiconductor will often be of use in the method of the invention.

Other types of diode which could be used in the method of the invention include:

Junction diodes

Schottky diodes

PIN (P-Intrinsic-N) diodes

FET diodes

Avalanche diodes

Camel diodes

Tunnel diodes

Impatt diodes

Point contact diodes

Metal Oxide Semiconductor diodes

Metal-Insulator-Semiconductor diodes

Metal-Insulator-Metal diodes, and these may be manufactured using any suitable semiconductor material, for example silicon, germanium, gallium arsenide, bismuth or any other Group III or Group IV element.

The size of the diodes will depend on the sample conditions under which the target species or the diode is to be detected.

The electrical signal passed through the sample may be sinusoidal. A high-frequency signal in the MHz range may be employed to advantage. The amplitude selected for the applied signal will also depend on the conditions in which the method is employed.

The diode junction(s) may need to be driven into forward conduction by the electrical signal, in order for the presence of the diode junction(s) to modify the signal. Thus, the voltage across each diode when the signal is passed through the sample will need to be equal to a significant fraction of the forward conduction voltage (usually referred to as Vbe) of the diode.

The modification of the signal waveform by the diode junction(s) will be the creation of or the enhancement of, frequencies in the signal which are harmonics of the fundamental frequency of the signal. Any generation of or increase in amplitude of these harmonics will indicate the presence in the sample of rectifying components. If many diodes are introduced into the mixture of species from which a sample is taken, the waveform change will provide an indication of the number of diodes which are present in the sample and hence can be indicative of the number of the target species present in the sample or in the original mixture.

Because it is necessary to detect the presence of harmonics in the modified waveform, the signal to be passed through the sample is preferably processed, as by filtering, so as substantially to remove all harmonics from the signal to ensure that the signal applied to the sample is a pure sine wave.

The harmonic content of the signal waveform may be analysed using a spectrum analyser. The signal waveform may be examined to see if a harmonic content greater than a predetermined level is present, or the waveform may be compared with that of the signal applied to the sample. Alternatively, the signal waveform may be compared with the waveform of the same input signal after it has been passed through a conductive fluid or sample containing no electrical diodes. In any event the extent of the modification of the signal due to the presence of diodes in the sample can be determined.

The sample containing the diode(s) will commonly but not essentially be capable of conducting an alternating electrical current. A suitable conductive fluid, for instance saline solution, may therefore be added to the sample prior to passing the electrical signal through the sample.

Alternatively, however, the invention may be applied to a non-conductive fluid sample such as air containing the diode, the signal generator producing the required alternating electrical signed being capacitative coupled to said diode through the non-conductive medium.

One way in which it may be ensured that the presence of diodes in the sample is dependent on the presence of the target species in the sample is by coating the diodes with a binding species capable of reacting specifically with the target species, so that the target species present in the mixture into which the diodes are introduced binds to the binding species. Any diodes which remain unbound to the target species are then removed from the mixture or the sample before the electrical signal is passed through the sample.

Thus, according to a first version of the invention, there is provided a method of detecting the presence of a target species in a sample consisting of a mixture of species, comprising the steps of introducing into the sample one or more electrical diodes having a coating of a binding species capable of reacting specifically with the target species, so that the target species present in the sample binds to the binding species; removing or separating from the sample diodes which are not bound to the target species; passing an alternating electrical signal having a known waveform through the sample and detecting the modification of the waveform of the signal emerging from the sample due to the presence of a diode or diodes in the sample.

The preferred form of diode used in this first version of the invention is a simple lump of a PN-doped semiconductor, although other types of diode would also be of use in the method.

If a quantitative indication of the number of target species present in the sample is to be obtained, the number of diodes added to the sample will preferably be such that an excess of the binding species, relative to the amount of the target species present, is introduced into the sample.

Diodes which are not bound to the species may be removed from the sample in any appropriate manner. Alternatively, they may be "separated" from the sample, by which is meant that the unbound diodes are made to migrate to, and held in position in, a region of the sample from which their presence will not affect the electrical signal passed through the sample. Such a separation could be achieved, for instance, by magnetic or by mechanical means.

The target species detected by this method of the present invention may, for example, be an antibody. The binding species coating the electrical diode(s) will in that case conveniently be an antigen capable of binding specifically to the target antibody. In such a situation, the electrical diode(s) will conveniently be of the order of 0.3–5.0 micrometers in any particular dimension to allow effective binding to the target antibody to occur.

According to a preferred feature of the first version of the invention the target species, once bound to the binding species coating a diode, is fixed in position in a vessel containing the sample, so that unwanted species can be removed or separated from the vessel prior to passing the electrical signal through the mixture. Many suitable methods of fixing the target species into position are known. For instance, in the case if an immunological assay, in which the presence of a target antibody is to be detected, a so-called "sandwich" assay technique may be used. In this technique, the inside walls of the vessel are coated with a supporting reagent capable of binding specifically to the target species. Any target species present in the sample are therefore bound to the inside walls of the vessel and, on introduction of electrical diodes, a number of such "sandwiches", each comprising the supporting species, the target species and the binding species coating a diode, is formed. The vessel can then, for instance, be washed to remove unwanted reagents, filled with a suitable conductive fluid such as saline solution, and an electrical signal passed through the fluid in accordance with the method of the invention. In such a method, the amount of target species present in the original sample will determine the number of diodes which remain supported in the vessel after washing and hence the extent of the modification of the signal passed through the conductive fluid.

According to the present invention there is therefore also provided a method of detecting the presence of a target species in a sample consisting of a mixture of species, comprising the steps of: fixing the target species in a pre-determined region of a vessel in which the sample is contained; introducing into the sample an electrical diode or diodes having a coating of a binding species capable of reacting specifically with the target species, so that the target species present in the sample binds to the binding species and hence fixes the diode or diodes in the predetermined region of the vessel; removing or separating from the vessel or from a particular region of the vessel any unwanted species, including any diodes which are not bound to the target species; introducing into the vessel an electrically conductive fluid; passing an alternating electrical signal having a known waveform through the fluid; and detecting the modification of the waveform emerging from the fluid due to the presence of a diode or diodes in the fluid.

The target species may be fixed to a predetermined region of the vessel by coating the predetermined region of the inner wall of the vessel with a supporting species capable of reacting specifically with the target species.

Another way in which it may be ensured that the presence of diodes in the sample is dependent on the presence of the target species in the sample is by introducing the target species into the mixture of species together with the diode or diodes. Such a technique might be used, for instance:

a) where the target species is added to the mixture and it is desired to monitor the movement of the target through the mixture; or b) where the target species is one of a number of species present in a mixture in a system and the diode or diodes are also present in the mixture, and it is desired to detect whether the mixture has leaked out of the system.

Thus, according to a second version of the invention there is provided a method of detecting the presence of a target species in a sample taken from a mixture of species, where any target species present in the mixture has been introduced into the mixture from a source, comprising the steps of introducing into the source of the target species, before the sample is taken from the mixture, one or more electrical diodes, such that if the target species is present in the mixture then diodes will also be present in the mixture; passing an alternating electrical signal having a known waveform through the sample; and detecting the modification of the waveform of the signal emerging from the sample due to the presence of a diode or diodes in the sample.

The sample may be taken from the mixture at a particular location relative to the source of the target species. The presence or absence of the target species in the sample would then provide information on the movement of the target species through the mixture from its source.

Alternatively, the source of the target species may be a system from which leaks are desired to be detected, the sample then being taken from a location outside the system. The presence of the target species in such a sample would indicate a leak from the system.

In a similar manner, the presence of pollutants in an environment, which may have entered that environment from a particular identified source, may be detected if diodes are introduced into that source.

The present invention accordingly provides a method of monitoring the movement of a target species through a system containing a mixture of species, comprising the steps of removing a sample of the mixture from a particular location in the system relative to the point at which the target species was introduced into the system; and detecting the presence of the target species in the sample using the method of detecting provided by the present invention.

The invention also provides a method of detecting the presence or absence of a leak in an otherwise closed system containing a target species, comprising the steps of taking a sample from a location outside the system; and detecting the presence or absence of the target species in the sample using the method of detecting provided by the present invention.

The present invention additionally provides apparatus for detecting the presence of a target species in a sample taken from or consisting of a mixture of species, comprising: a test chamber for containing the sample; means for generating and passing through the test chamber an alternating electrical signal having a known waveform; an electrical diode or diodes capable of introduction into the sample contained in the test chamber; and means for detecting any modification of the waveform of the signal emerging from the test chamber attributable to the presence of rectifying junctions in the sample under test.

The apparatus may include filter means for removing harmonic frequencies from the signal to be applied to the test chamber so that the signal to be applied is essentially sinusoidal in waveform.

More specifically, and for use in the method provided the first version of the invention, the invention provides apparatus for detecting the presence of a target species in a sample consisting of a mixture of species, comprising: a test chamber for containing the sample; means for generating and passing through the test chamber an alternating electrical signal having a known waveform; an electrical diode or diodes having a coating of a binding species capable of reacting specifically with the target species, the diode or diodes being capable of introduction into the sample contained in the test chamber; and means for detecting any modification of the waveform of the signal emerging from the test chamber attributable to the presence of rectifying junctions in the sample under test.

The invention will now be described by way of example and with reference to the accompanying drawings, in which.

DETAILED DESCRIPTION OF THE DRAWINGS

Figure 1:
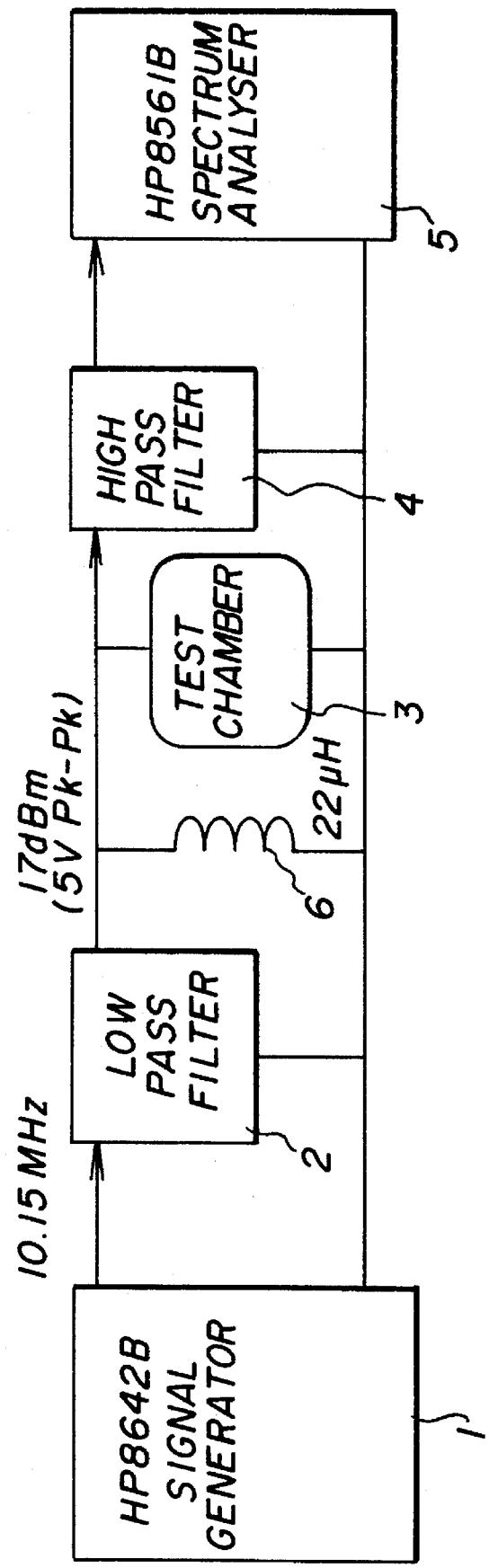
FIG. 1 is a block diagram of experimental apparatus used to investigate the method of the present invention.
Figure 3:
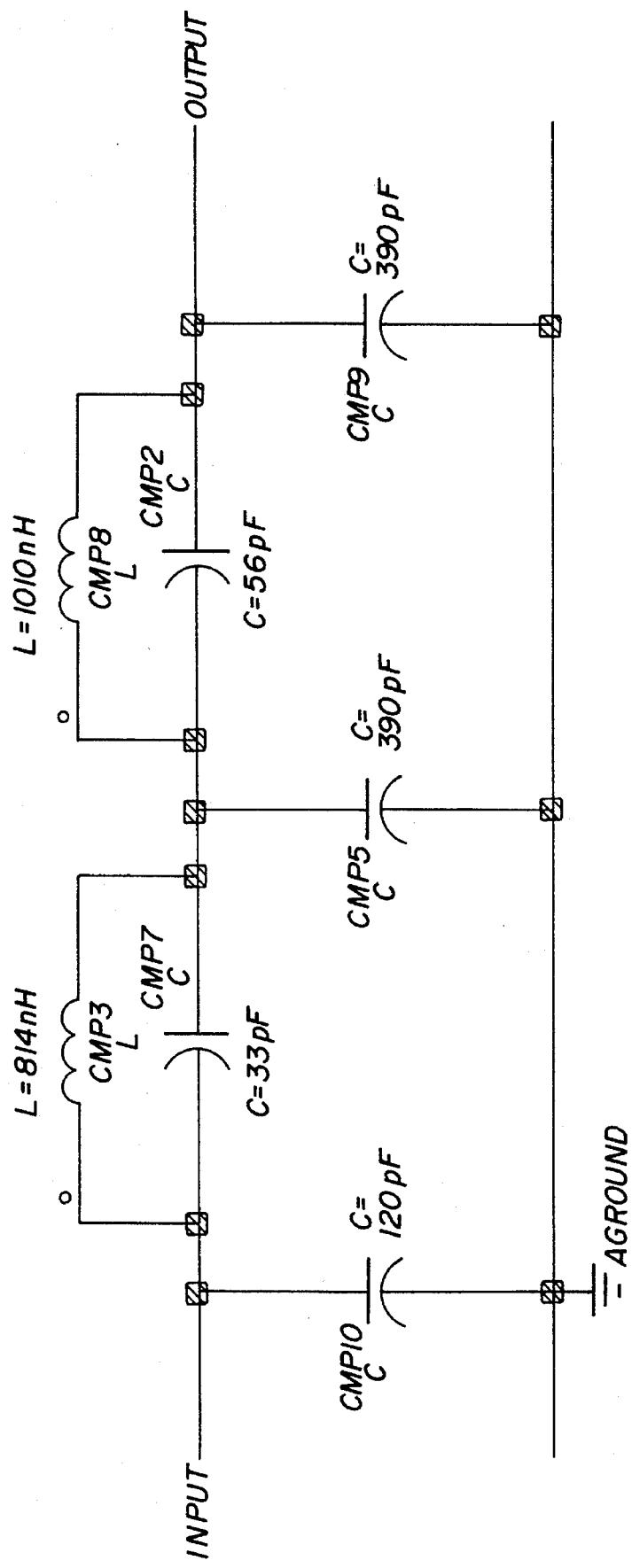
FIGS. 3 and 4 show the detailed construction of the low- and high-pass filters respectively of the apparatus shown in FIG. 1.
Figure 4:
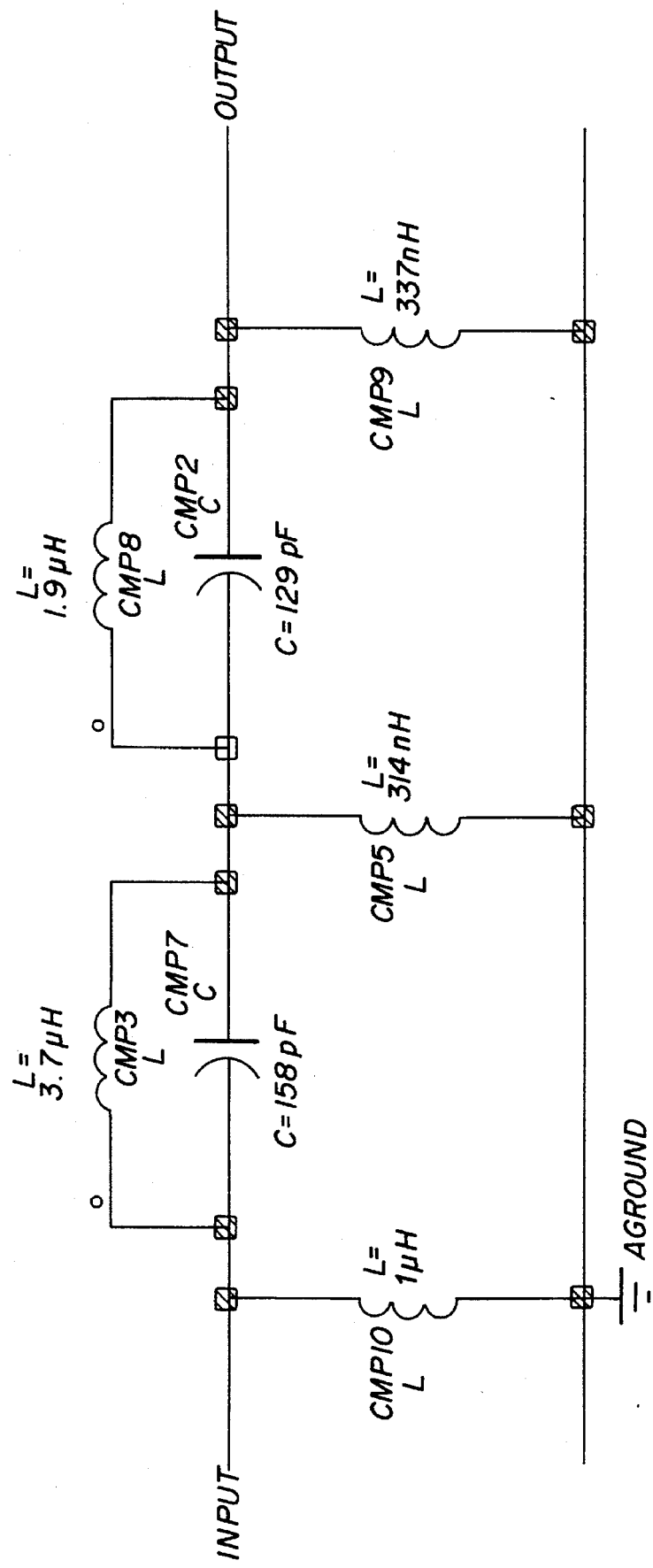
Figure 5:
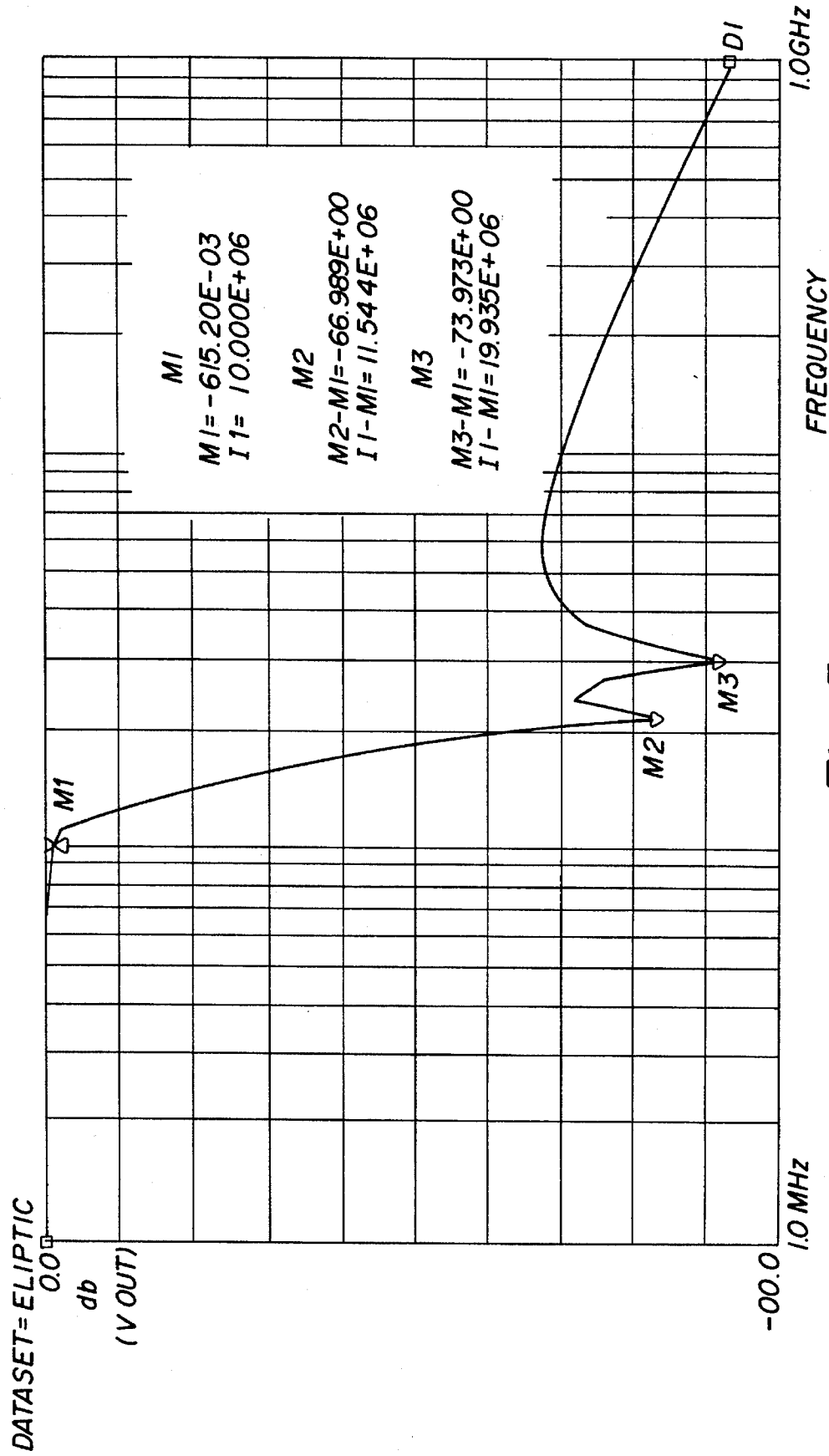
FIGS. 5 and 6 show the frequency responses of the low- and high-pass filters respectively.
Figure 6:
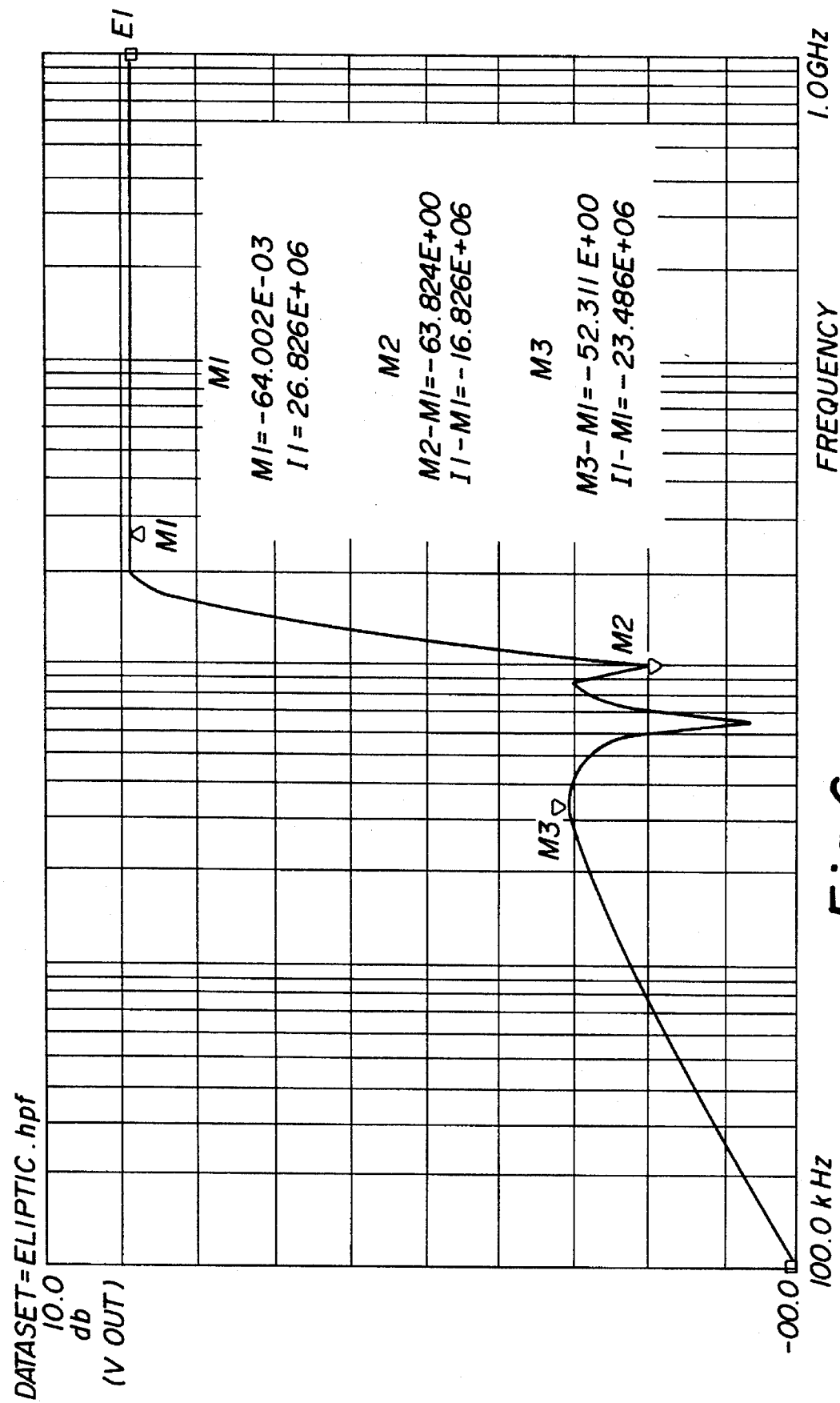

An experiment was performed, using the apparatus shown schematically in FIG. 1 in order to demonstrate the method of the present invention. The apparatus comprises an HP8642B signal generator 1 used to pass an alternating electrical signal through the test chamber 3; a low-pass filter 2 (the construction and characteristics of which are illustrated in FIGS. 3 and 5 respectively) by means of which the harmonic content of the signal generator's output signal is substantially attenuated; a high-pass filter 4 (the construction and frequency response characteristics of which are shown in FIGS. 4 and 6 respectively); and an HP8561B spectrum analyser 5.

The spectrum analyser was connected to the test chamber via the high-pass filter in order to remove or substantially attenuate the fundamental frequency of the signal generator output signal from the signal input to the spectrum analyser 5. This prevented the fundamental frequency signal from overloading the analyser's input stage.

A 22 uH inductor 6 was added across the chamber to maintain a DC datum without shunting the high-frequency signals.

Signal generator 1 was used to generate a 10.15 MHz signal having a peak-to-peak amplitude of 5 V. This signal was passed, via filter 2, to the test chamber 3, which is shown in more detail in FIG. 2.

Figure 2:
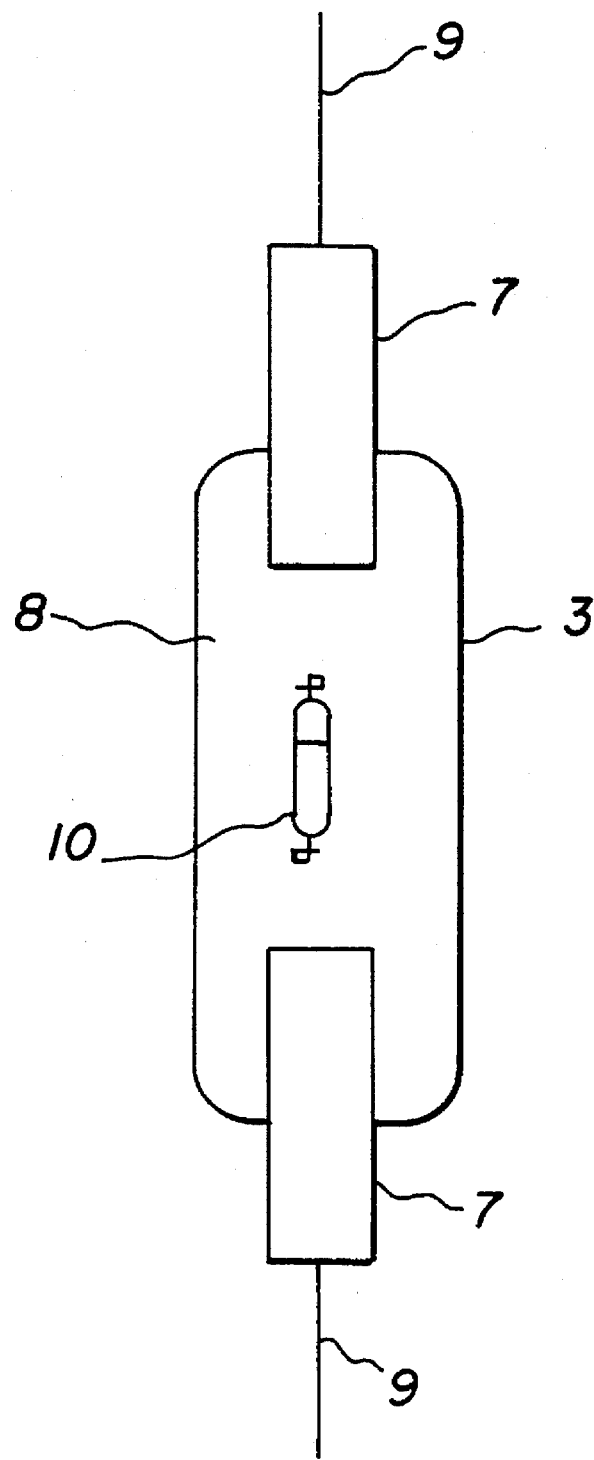
FIG. 2 is a schematic cross-section through the test chamber of the apparatus shown in FIG. 1.

The chamber 3, semi-cylindrical in section and of length 52 mm and diameter approximately 6 mm, contained steel electrodes 7 in a saturated saline solution 8. The electrodes were the screw ends of M4 steel bolts, and were spaced approximately 16 mm apart, their spacing being adjustable from each end by means of the screw-thread of each electrode. Connections 9 led to the circuitry illustrated in FIG 1. Measurements could be conducted on the test chamber either when it contained saline solution only or when it contained a diode. In FIG. 2, the chamber is shown containing a 1N4148 diode 10 having shaped, cropped leads 8 mm apart.

Figure 7:
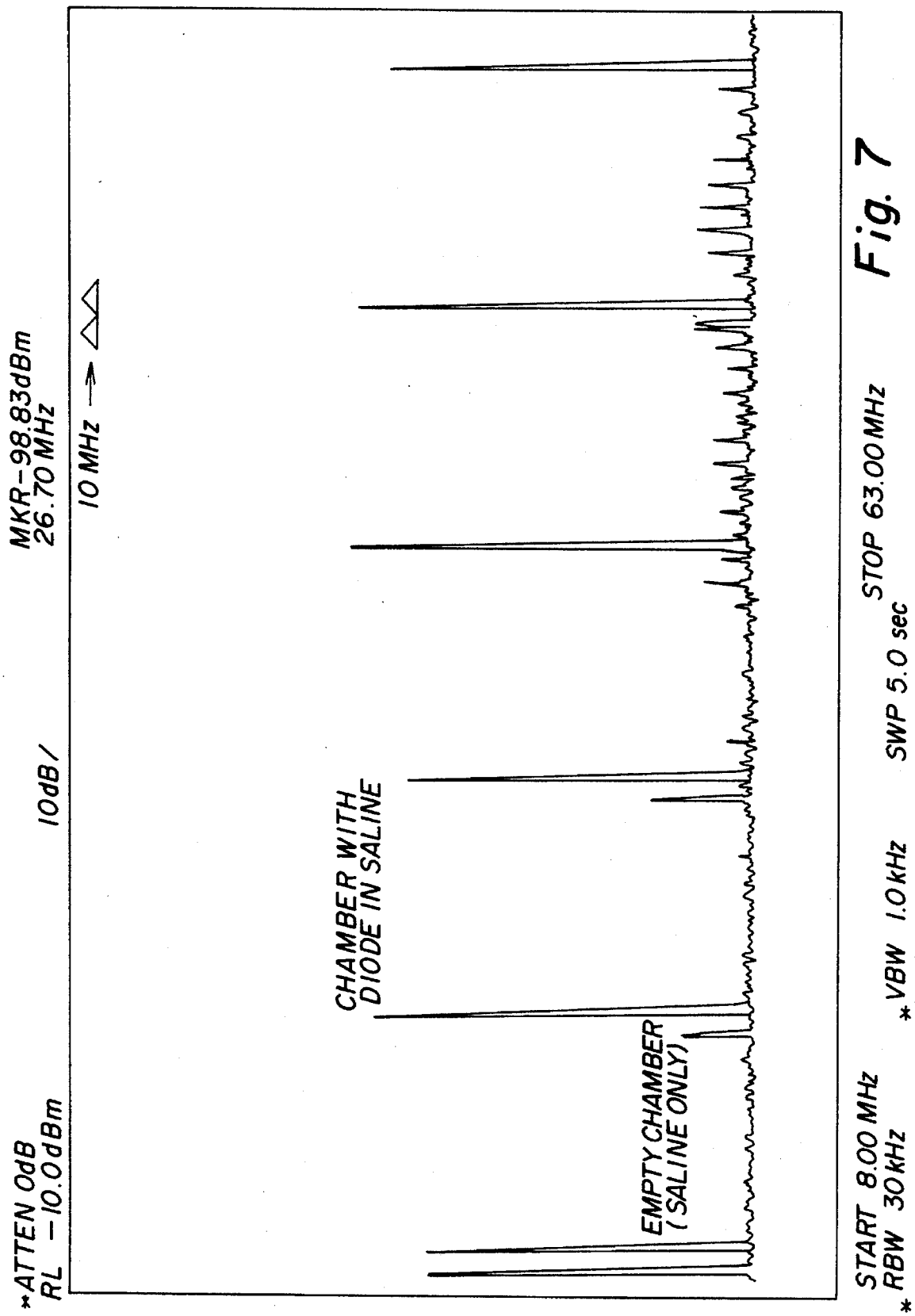
FIG. 7 shows the results of an experiment conducted using the apparatus of FIGS. 1–6.

In the experiment conducted, the signal generated at 1 was passed through the test chamber 3 and recorded by the spectrum analyser 5, firstly with only saline solution inside the test chamber and secondly with a 1N4148 diode (a general purpose silicon diode) introduced into the saline solution. The traces obtained from the analyser for these two situations are shown together in FIG. 7, which shows the amplitude readings from the spectrum analyser, in the range of 8 to 63 MHz. Two sets of peaks are shown on the plot, offset by a small amount for legibility. The left-hand peaks represent the test chamber containing saline only. The right-hand peaks represent the response with the diode present. It can be seen that the 10.15 MHz fundamental remained substantially unchanged, but the harmonics present in the original signal showed an increase in signal strength of 30 to 45 dB when the diode was present.

The results of this experiment clearly demonstrate the way in which an a.c. signal passing through a conductive fluid can be modified by the presence in that fluid of a rectifying device such as a semi-conductor diode. The non-linear characteristics of the diode result in the generation and/or enhancement of harmonics, the presence of which can be detected to provide a clear indication of the presence of the diode in the fluid.

In accordance with the first version of the invention, if the diode in the fluid is bound to a target species, the presence of which in the fluid is to be detected, detection of the presence of the diode, by reference to its effect on current passing through the fluid, enables detection of the presence of the target species.

The method of the invention may be used for example to detect the presence of an antibody X in a reaction mixture. The apparatus used would be essentially the same as that shown in FIGS. 1 and 2, with appropriate modification due to the scale on which immunoassay-type reactions are generally carried out. For instance, for the purpose of immunoassays, the diodes used would have to be as small as possible for effective binding to the antibody. Overall sizes of the order of 0.3 to 5.0 micrometers in any particular dimension are envisaged.

For rectification of the electrical signal to occur, the diodes must be driven into forward conduction. This requires a voltage across each diode equal to some significant fraction of its Vbe. It follows that the field strength in the saline or other conductive fluid used needs to be of the order of 1 volt per micrometer and that the electrode spacing needs to be of the order of a few multiples of the diode size to keep the electrode voltage to a manageable value.

The test can be performed as follows. The reaction mixture containing target X is introduced into a test chamber, the inside walls of which-are coated with an antigen Z which binds specifically to one region of X. Any antibodies X present in the mixture will react with antigen Z thereby to be held in position, as ZX pairs, the chamber walls.

A number of diodes previously coated with an antigen Y which binds specifically to another region of antibody X, are then introduced into the reaction mixture containing X. The number of diodes so introduced should be such that an excess of antigen Y is present in the mixture so that any target antibody present in the mixture will be bound to Y on the surface of a diode. This will result in the creation of Z-X-Y "sandwich" groups supported on the internal walls of the test chamber.

The chamber can then be washed out with a suitable solvent so as to remove unwanted species and leave only a coating on the internal walls of the chamber of the Z-X-Y sandwich groups. Diodes, the coating of which has not reacted with target antibodies, will also be removed by the washing process because they will not be fixed to the chamber walls.

The test chamber is then filled with saline or some other appropriate conductive fluid, and an electrical signal passed through the chamber as described in the example above. Modification of the signal, by the creation or enhancement of harmonics, indicates the presence of at least one diode in the chamber, and hence of the target antibody X in the original reaction mixture. The extent of the modification, for instance compared to that detected using a test solution containing a known concentration of X, indicates the quantity of X present in the original mixture.

Another way in which the method of the invention may be used, for example, is to monitor leaks of substances, in particular toxins and other pollutants, into the environment. In such a case, a large quantity of microdiodes would be added to a fluid in a pipe, or to a gas in an exhaust stack, from which pipe or stack any leaks were to be detected. Any leak of the fluid or gas into the environment surrounding the pipe or stack would be accompanied by a corresponding loss of microdiodes from the pipe or stack.

An appropriate sample would then be removed from a location near to the pipe or stack, for instance, an air sample or a sample of water from a nearby waterway into which it is suspected that the pollutant is leaking, and the method of the invention would then be used to detect the presence in that sample of microdiodes, and hence also of the leaked pollutant itself.

It is possible, using the methods of the present invention, to detect extremely small concentrations of a target species in a simple and efficient manner, and this detection method is likely to find wide applicability in all areas of science and industry.

I claim:

1. A method of detecting the presence of diodes in a liquid, comprising the steps of passing an alternating electrical signal having a known waveform through the liquid, and detecting the modification of the waveform of the signal emerging from the liquid, said modification of the waveform being due to the presence of the diodes in the liquid.

2. A method according to claim 1, in which the electrical signal passed through the sample is a sinusoidal high-frequency signal in the MHz range.

3. A method according to claim 1, in which junctions of the diodes are driven into forward conduction by the electrical signal, thereby to modify said signal by the creation of, or the enhancement of, frequencies in the signal which are harmonics of the fundamental frequency of the signal.

4. A method according to claim 3, in which the harmonic content of the signal waveform is analysed using a spectrum analyser.

5. A method according to claim 3, in which, in order to detect the presence of harmonics in the modified waveform, the signal to be passed through the sample is processed in a manner substantially to remove all harmonics from the signal, thereby to ensure that the signal applied to the sample is a pure sine wave.

6. A method according to claim 5, in which the signal to be passed through the sample is processed by filtering to remove harmonics.

7. A method according to claim 1 in which the sample comprises a conductive fluid.

8. A method according to claim 1, wherein the sample comprises a non-conductive fluid, and wherein a signal generator produces the required alternating electrical signal, and wherein the alternating electrical signal is capacitively coupled to the diodes through the non-conductive medium.

9. A method for detecting the presence of a target species in a sample containing a mixture of species including a biochemical reaction which involves a specific reaction of the target species to form a reagent-target pair, said method comprising the steps of:

introducing electrical diodes bound to a binding species, said binding species participating in said biochemical reaction, into the sample in such a manner that the presence of the diodes in the sample is dependent on the presence of the target species in the sample;

removing or separating diodes which are not bound to the target species:

passing an alternating electrical signal having a known waveform through the sample; and detecting a modification of the waveform of the signal emerging from the sample, said modification of the waveform being due to the presence of diodes in the sample, the presence of the target species in the sample being derived from the detected modification of the waveform.

10. A method according to claim 9, in which the diode is coated with the binding species capable of binding specifically with the target species.

11. A method according to claim 9, further comprising the steps of:

fixing the target species by a binding species in a predetermined region of a vessel in which the sample is contained;

introducing into the sample the electrical diodes bound to a binding species whereby the biochemical reaction of the target species occurs forming the reagent-target pair, and hence fixes the diodes in the predetermined region of the vessel;

removing or separating from the vessel or from a particular region of the vessel any diodes which are not bound to the target species;

introducing into the vessel an electrically conductive fluid;

then performing the steps of passing the alternating electrical signal through the fluid and detecting the modification of the waveform, wherein the presence of the target species in the sample is derived from the detected modification of the waveform.

12. A method according to claim 9, in which the electrical signal passed through the sample is a sinusoidal high-frequency signal in the MHz range.

13. A method according to claim 9, in which junctions of the diodes are driven into forward conduction by the electrical signal, thereby to modify said signal by the creation of, or the enhancement of, frequencies in the signal which are harmonics of the fundamental frequency of the signal.

14. A method according to claim 13, in which the harmonic content of the signal waveform is analysed using a spectrum analyser.

15. A method according to claim 13, in which, in order to detect the presence of harmonics in the modified waveform, the signal to be passed through the sample is processed in a manner substantially to remove all harmonics from the signal, thereby to ensure that the signal applied to the sample is a pure sine wave.

16. A method according to claim 15, in which the signal to be passed through the sample is processed by filtering to remove harmonics.

17. A method according to claim 9 in which the sample comprises a conductive fluid.

18. A method according to claim 9, wherein the sample comprises a non-conductive fluid, and wherein a signal generator produces the required alternating electrical signal, wherein the alternating electrical signal is capacitively coupled to the diodes through the non-conductive medium.

19. A method of monitoring the movement of a target species introduced into a system, said method comprising the steps of:

removing a sample of the mixture from a particular location in the system relative to the point at which the target species was introduced into the system;

introducing electrical diodes bound to a binding species into the sample in such a manner that the presence of the diodes in the sample is dependent upon the presence of the target species in the sample, said binding species binding to said target species;

passing an alternating electrical signal having a known waveform through the sample; and detecting a modification of the waveform of the signal emerging from the sample, said modification of the waveform being due to the presence of diodes in the sample, wherein the presence of the target species in the sample is derived from the detected modification of the waveform.

20. A method of detecting the presence or absence of a leak in an otherwise closed system containing a target species, comprising the steps of:

introducing electrical diodes bound to a binding species having affinity for the target species into the system in such a manner that the presence of the diodes in the system is dependent on the presence of the target species in the system;

taking a sample from a location outside the system;

passing an alternating electrical signal having a known waveform through the sample; and detecting the modification of the waveform of the signal emerging from the sample, said modification of the waveform being due to the presence of diodes having a binding species which binds to said target species in the sample, wherein the presence of the target species in the sample is derived from the detected modification of the waveform.

21. Apparatus for detecting the presence of a target species in a liquid, comprising: a test chamber for containing the liquid; generating means for generating and passing through the test chamber an alternating electrical signal having a known waveform; and means for detecting any modification of the waveform of the signal emerging from the test chamber attributable to the presence of diodes in the liquid under test, wherein electrical diodes, bound to a binding species, are introduced into the sample contained in the test chamber, and are capable of binding with the target species.

22. Apparatus according to claim 21, including filter means coupled to said generating means, for removing harmonic frequencies from the signal to be applied to the test chamber so that the signal to be applied is essentially sinusoidal in waveform.

23. Apparatus for detecting the presence of a target species in a liquid, said apparatus comprising:

a test chamber for containing the liquid;

means for generating and passing through the test chamber an alternating electrical signal having a known waveform; and means for detecting any modification of the waveform of the signal emerging from the test chamber attributable to a presence of diodes in the liquid under test, wherein electrical diodes having a coating of a binding species capable of reacting specifically with the target species are introduced into the liquid contained in the test chamber.

* * * * *